US00PP15626P2

(12) United States Plant Patent
Dhyani et al.

(10) Patent No.: US PP15,626 P2
(45) Date of Patent: Mar. 8, 2005

(54) ***GLADIOLUS* HYBRID PLANT 'THE SAINT'**

(50) Latin Name: ***Gladiolus* hybrid**
Varietal Denomination: The Saint

(75) Inventors: Devendra Dhyani, Palampur (IN); Debasish Mukherjee, Palampur (IN)

(73) Assignee: Council of Scientific and Industrial Research, New Delhi (IN)

( * ) Notice: Subject to any disclaimer, the term of this patent is extended or adjusted under 35 U.S.C. 154(b) by 165 days.

(21) Appl. No.: 10/106,085

(22) Filed: Mar. 25, 2002

(51) Int. Cl.[7] ..... A01H 5/00
(52) U.S. Cl. ..... Plt./301
(58) Field of Search ..... Plt./301

*Primary Examiner*—Bruce R. Campell
*Assistant Examiner*—Michelle Kizilkaya
(74) *Attorney, Agent, or Firm*—Merchant & Gould P.C.

(57) ABSTRACT

The present invention relates to a novel hybrid plant named 'The Saint' and belonging to the family Iridaceae said plant is a cross between two *gladiolus* varieties, 'Purple King' and 'Friendship' and is an ornamental plant widely cultivated for beautiful flowers which are of commercial and export value, further said plant is propagated vegetatively by corms and hence can be maintained as a stable genotype.

1 Drawing Sheet

GENUS AND SPECIES OF THE PLANT CLAIMED AND VARIETY DENOMINATION

The present invention relates to a novel *Gladiolus* hybrid sp. variety named 'The Saint'. This new variety belongs to the family Iridaceae, genus *Gladiolus L*, and species *Gladiolus* sp. (*Gladiolus* hybrid). The novel plant being a hybrid, has been developed in a breeding programme. The novel plant 'The Saint' is propagated vegetatively by corms and hence can be maintained as a stable genotype. The plant of the invention is a cross between two *gladiolus* varieties, 'Purple King' (unpatented) and 'Friendship' (unpatented) and is an ornamental plant widely cultivated for beautiful flowers which are of commercial and export value.

BACKGROUND OF THE INVENTION

*Gladiolus* is a herbaceous bulbous plant grown for its beautiful flowers of different colour, shades and shapes throughout the world. *Gladiolus* belongs to the Family Iridaceae, Order Liliales and Class Monocotyledon.

*Gladiolus* is one of the important cut flowers throughout the world. The commercial cultivation is wide spread in temperate, tropical and subtropical climates. The demand of new varieties with better colour, quality flowers, and planting materials is always existing in the floriculture trade.

The modern garden cultivators *gladiolus* come from diverse genetic parentages. It has cumulative heterozygosity for many characters inherent with complex genetic constitution. In *gladiolus*, diverse parents are crossed together and the cultivars and the species that differ widely in chromosome numbers are also cross-fertile. In the present invention, the desirable strains obtained in $F_1$ generation were perpetuated vegetatively without being segregated in the following generations, so that the cultivars which are available today may be $F_2$, $F_3$ to $F_8$ or so of a particular cross further blended with some extra parents at nearly every generation. Thus they are not allowed to segregate freely in further generations because it is desirable to grow the plants asexually. Because of this reason, now the available modern cultivars have become so complex that the offspring obtained by crossing them, even two seedlings, do not appear similar

[(Misra, 1975) *Gladiolus* Br. Assn. Newsletter, No. 12, pp. 2–5].

The Applicants collected germplasm of different cultivars and hybrid varieties of *gladiolus* from National Botanical Research Institute Lucknow, India as per the list of *gladiolus* cultivars grown in India and described in the bulletin of '*gladiolus*' Economic Botany Information Service by Sharma et al. published by the Director National Botanical Research Institute Lucknow, 1988. Germplasm of *Gladiolus* was also collected from Netherlands in 1991 and various nurseries of Kalimpong, Darjeeling, West Bengal, India. The record of the collected germplasm of *gladiolus* was maintained in the accession register of the Floriculture Division of the Institute of Himalayan Bioresource Technology (IHBT), Palampur, India.

The applicants initiated a breeding program to develop better types of *gladiolus* hybrids suitable to wide range of climatic conditions, and having wide range of characteristics such as better colour, increased number of florets and spike length as per the international standards, better yield of corms and cormels, tolerant to the common diseases etc. The collected germplasm of *gladiolus* was planted in the experimental field of IHBT for their propagation and multiplication. In this breeding programme conventional breeding method (hybridization) was used. More than 100 cross combinations were made by using distinct varieties such as 'Oscar' (unpatented), 'Jester' (unpatented), 'Snow Princess' (unpatented), 'Eurovision' (unpatented), 'Ballerina' (unpatented), 'King Liar' (unpatented), 'Cherry Blossom' (unpatented), 'Her Majesty' (unpatented), 'Green woodpecker' (unpatented), 'Friendship' (unpatented), 'Vink's Glory' (unpatented), 'Aldebaran' (unpatented), 'Red Beauty' (unpatented), 'Top Brass' (unpatented), 'Copper King' (unpatented), 'Bonfire' (unpatented), 'White Goddess' (unpatented), 'Sunny Boy' (unpatented), 'Tropic Sea' (unpatented), and 'Friendship Pink' (unpatented), etc.

Color description of some of the parentage as described in NAGC Bulletin.

'Oscar'—Turkey red, throat blotched sulphur yellow.

'Green Woodpecker'—Pea Green, throat blotched pea green spotted ruby red.

'Eurovision'—Signal red, throat streaked pea green.

'Friendship Pink'—Dawn Pink, throat blotched pea green having splashes ruby red.

'Aldebaran'—Straw Yellow and throat bloched signal red.

'Friendship'—Clear pink with yellow throat.

'Jester'—Ruffled, deep Yellow petals and bright red blotches.

'Her Majesty'—Ruffled, Blue violet with darker edges and white throat.

'Snow Princess'—White.

'Eurovision'—Light Vermillion with white veins.

'Purple King'—Purple, rich in colour with white picottee edges, white marks deeper in the throat.

These parentage plants are grown in India for more than 25 years. Details regarding these plants have been published and these plants are available to the public.

As the aim is the production of seed of known parentage, emasculation in first three flowers in a selected spike is done before the opening of the flowers and stigma becomes receptive. Anthers are removed carefully from each flower. Emasculated flowers were covered with butter paper bags used for breeding purposes. Pollination was done in the emasculated flowers next day morning with in 24–30 hours with the pollens of the desired parents in the month of April–May 1992. The seeds were collected from mature pods in the month of July–August 1992 and were sown in beds under open field conditions and covered with dry grasses for moisture preservation in December 1992. The resultant seedlings were space planted in the field at Palampur in March–April 1993.

Many seedlings came out from a single cross combination. These plants were critically evaluated and tagged as per the desired colour combinations, growth and flowering parameters. The corn and cormels of the selected hybrid plants were replanted continuously four years in the filed for further evaluation and multiplications. Based on the superior performance for attractive colour combination, compactness of flower spike, number of flowers per spike, length of flower spike, Number of corm and cormels per plant evaluation and selection of superior quality hybrids were made.

Thus, the breeding program involved hybridisation of commonly available *gladiolus* plants. In other words, the hybrids were developed by crossing parental genotypes involving sexual hybridization in the breeding programme.

The program yielded a number of hybrid plants out of which one genotype namely IHBT-GH-253 was selected and christened as 'The Saint'. The plant is a hybrid between 'Purple King' and 'Friendship'. This plant was found to have new colour, flower size, number of florets per spikes, length of flower spikes, better yield of corm and cormels and less prone to common diseases. Growing the plant on a commercial scale offers the horticulturists an improved and new variety, which can be commercially cultivated.

OBJECTS OF THE INVENTION

The object of the present invention is to provide a new *gladiolus* genotype christened as 'The Saint'.

SUMMARY OF THE INVENTION

The present invention relates to a novel hybrid plant named 'The Saint' and belonging to the family Iridaceae. The novel plant being a hybrid, has been developed in a breeding programme. The novel plant 'The Saint' is propagated vegetatively by corms and hence can be maintained as a stable genotype. The plant of the invention is a cross between two *gladiolus* varieties, 'Purple King' and 'Friendship' and is an ornamental plant widely cultivated for beautiful flowers which are of commercial and export value.

BRIEF DESCRIPTION OF THE ACCOMPANYING DRAWING

FIG. 1 is a photograph of field grown flower spike of IHBT-GH-253 ('The Saint') depicting decorative type flowers of Shrimp Red (RHS-33C) with Vermilion (RHS-41A) colour on center of the lip petals. The illustrated flower spike is from a generation of the variety grown in 1992. The plant giving rise to this flower spike was grown under open field conditions in Palampur area of Himachal Pradesh. Palampur is at 1300 m above main sea level, which comes under sub-humid, sub-temperate zone and having average maximum and minimum temperature of 30° C. and 10° C., respectively. The average annual rainfall is approximately 250 cm.

DETAILED BOTANICAL DESCRIPTION

Thus, the invention provides a new genotype christened as 'The Saint'. This plant has been developed through planned breeding experiments conducted at Institute of Himalayan Resources, (IHBT) Palampur, Himachal Pradesh, India with defined aim to develop superior *gladiolus* genotypes. For this purpose, *gladiolus* varieties were collected from different sources and grown in the fields at Palampur, India for facilitating breeding program. The emasculation and pollination in different varieties were carried out during the months of April–May 1992. The seeds were collected in July–August 1992 and sown in beds under open field conditions and covered with dry grasses in December 1992. The resultant seedlings were space planted in the field at Palampur in March–April 1993. The corms and cormels of surviving hybrid plants were replanted continuously four years for screening and multiplication.

Based on the superior performance for attractive colour combination, compactness of flower spikes, number of flowers per spikes, length of flower spikes, number of flowers remaining open at a time, number of corm and cormel production per plant, the plant of this invention (IHBT-GH-253) was selected for further observation and evaluation.

Considering the superior characteristics like excellent colour, number of flowers, compactness of flower spikes, plant height, ruffled-ness of flower petals, regeneration potential and freedom from common diseases, it was asexually reproduced through corm and cormels to maintain purity.

The selected hybrid IHBT-GH-253 was christened as 'The Saint' and grown at row distance of 30 cm and plant to plant distance of 15 cm for four consecutive years to study its growth and flowering performance and multiplication. Data were recorded on randomly selected twenty plants every year. The hybrid IHBT-GH-253 maintained uniformity in its growth and flowering performance.

Evidence of Uniformity and Stability

The hybrid IHBT-GH-253 has remained stable and uniform for its morphological characters and showed consistency in performance for various growth and flowering parameters during its evaluation and vegetative multiplication since 1993. Throughout the evaluation period of IHBT-GH-253 no variants were found from the normal population.

Statement of Distinction

The genotype IHBT-GH-253 possesses standard bi color decorative type flowers of Shrimp Red (RHS-33C) with Vermilion (RHS-41A) colour on center of the lip petals. The flower petals are slightly ruffled which is quite clear from FIG. 1.

The genotype IHBT-GH-253 is distinct in regeneration potential.

The plant of invention 'The Saint' is thus a new and distinct hybrid plant, having the following combination of characters:

| | | |
|---|---|---|
| (a) | Type | Decorative |
| (b) | Days to flower | 84 days |
| (c) | Number of spikes/plant | 2.11 |
| (d) | Length of the flower spike | 108 cm |
| (e) | Number of flowers/spike | 15.9 |
| (f) | Flower colour | Shrimp Red (RHS-33C) with Vermilion (RHS-41A) colour on center of the lip petals. |
| (g) | Type of petals | Petals lightly ruffled. |
| (h) | Number of flowers that remain open at a time | 7.0 |
| (i) | Longevity of the 1st flower | 2.70 days |
| (j) | Diameter of 1st flower | 10.9 cm |
| (k) | Longevity of the spike | 7.49 days |
| (1) | Number of corms/plant | 2.08 |
| (m) | Diameter of corms | 6.07 cm |
| (n) | Number of cormels/plant | 135.8 |

Objective Description of the Genotype 'The Saint'

The following is an objective description of the new variety:

| | | |
|---|---|---|
| 1. | Genus: | *Gladiolus* |
| 2. | Species: | Hybrid sp. |
| 3. | Family: | *Iridacae* |
| 4. | Order | *Liliales* |
| 5. | Class | *Monocotyledon* |
| 6. | Common name: | *Gladiolus*/Sword Lily |
| 7. | Plant height: | 126.7 cm |
| 8. | Growth habit: | Erect, uniform |
| 9. | Stem diameter: | 1.02 cm |
| 10. | Number of leaves/plant: | 6.98 |
| 11. | Height of leaves: | 58.0 cm |
| 12. | First flowering: | 84.1 days |
| 13. | Type of flowers | Decorative |
| 14. | Number of spikes/plant | 2.11 |
| 15. | Length of the flower spike | 107.9 cm |
| 16. | Number of flowers/spike | 15.9 |
| 17. | Flower colour | Shrimp Red (RHS-33C) with Vermilion (RHS-41A) colour on center of the lip petals. |
| 18. | Type of petals | Petals lightly ruffled |
| 19. | Number of flowers that remain open at a time | 7.0 |
| 20. | Longevity of the 1st flower | 2.70 days |
| 21. | Diameter of 1st flower | 10.9 cm |
| 22. | Longevity of the spike | 7.49 days |
| 23. | Number of corms/plant | 2.08 |
| 24. | Diameter of corms | 6.07 cm |
| 25. | Number of cormels/plant | 135.8 |
| 26. | Parentage | Purple King and Friendship |
| 27. | Growing Conditions | The plants are grown at open sunny sites and can be grown in a wide variety of soils. However, they require deep, well-drained sandy loam soils having pH around 6.0 to 7.0 for proper growth and flowering. |
| 28. | Temperatures | the day temperature could be between 15° C. to 20° C. |

-continued

| | | |
|---|---|---|
| 29. | Leaves | In a mature plant, leaves are attached to the stem in opposite fashion and have dark green colour |
| 30. | Number of leaves | 5 to 9 |
| 31. | Shape of the leaves | The leaves are sword-shaped phyllode, clustering at the swollen stem base, equivalent in 2-ranks, prominently ribbed, radical and cauline. |
| 32. | Description of reproductive parts | Flowers 2-whorled with six perianth segments, attached to a funnel-shaped cup shaping into a bent floraltube, hermaphrodite, trimerous, irregular, medianly zygomorphic, sessile and often protandrous and epigynous, born to one side on a simple or branched inflorescence subtended by two lanceolate, leaf-like valves. The flower is somewhat tubular and possesses six, coloured perianth segments (sepals and petals together), arranged in two whorls. The inflorescence is a spike, with the flowers arranged on the central axis in a single or two rowed symmetrical display, progressing from base to tip. Stamens 3, placed opposite to the outer whorl of the petals, extrose, epiphyllous, inserted below throat, bithecous, dehiscing by vertical slits, filaments distinct and basifixed. Gynoecium tricarpellary and syncarpous, having inferior ovary with axile placementation; style long, slender and simple with typically hinge-like creased trifid stigma and petaloid. |
| 33. | Fruits and Seeds | Fruits oblong-ellipsoid to obtusely triangular, loculicidal capsule with 3 chambers each having 2 rows mostly with winged seeds. |
| 34. | Fragrance | No Fragrance |
| 35. | Mode of reproduction. | Vegetatively by corms and cormels. |

The variety 'The Saint' can be characterized its stem color. The exposed first internode below the first flower has color Lettuce Green RHS-144A, and the rest of the stem covered with the leaf sheath has color RHS-145B.

The variety 'The Saint' can be characterized by its leaves. The leaves of variety 'The Saint' are numerous, cauline, alternately overlapped, and base sheathed. The leaf blades are narrow, linear-lanceolate, and sword shaped. The leaves have length of 31.5 cm–75.3 cm (average 60.53 cm) and width of 2.4–4.5 cm (average 3.29 cm). The leaves are cuneate or narrow at the base with an acute or acuminate apex. The venation of the leaves is parallel, the ribs strong and glabrous, and green in colour. The leaves have a margin that is entire and raised. Both surfaces are smooth and glabrous and scabrid due to fibrous ribs. The leaves are generally of color green (RHS-137B).

The variety 'The Saint' can be characterized by its perianth. The perianth of variety 'The Saint' is petaloid. The perianth has 6 tepals, arranged in two whorl, with 3 in each whorl. The perianth can be characterized as polyphyllous, shortly stalked or sessil, with sub-cordate or narrow base, obtuse at the top, oblong, oblanceolate, margin oblique entire, 2.8–5 cm×4.5–7.0 cm, and with imbricate aestivation.

The variety 'The Saint' can be characterized by bud size and colour. The colour of flower bud is Indian Orange (RHS-32 A). Buds are 4.70 cm to 6.50 cm long (bottom 3 bud were taken) and the average size 5.46 cm long. The diameter of the lower 3 buds ranges from 1.16 cm to 1.39 cm, and the average of 20 buds is 1.09 cm.

The variety 'The Saint' can be characterized by its reproductive organs. For example, the androecium can be characterized as having 3 stamens, as being triandrous, epiphyllous, arranged in a whorl, shorter than tepals and styles. The androecium has filaments that are terminal, pinkish-white at the top, about 3.0 cm long, anthers bibbed, dithecous, yellow-violet coloured, about 1.5 cm long, extrose, basifixed.

The variety 'The Saint' can be characterized by its gynoecium. For example, the gynoecium can be characterized by ovary tricarpellary, syncarpus, tribocular, inferior, many ovules in each locule, placentation axile; style filiform, terminal, slightly curved at the top, pale-white glandular c̲ 7.0 cm long stigma 3-lobed, stalked, each lobe bifid, petaloid, pale-white c̲ 3 mm long.

The variety 'The Saint' can be characterized by its plant disease resistance and/or susceptibility. Some incidence of Fusarium rot was noticed in the field as well as in the storage. This may be due to the high rainfall during the crop development period, because crop remains in the field during monsoon. But this variety 'The Saint' is performing better than its parent and many other varieties such as Hunting Song, Fidelio, Her Majesty, Oscar, Red Beauty, etc., in this region with respect to disease incidence.

This hybrid 'The Saint' produces 2.08 corm and 136 cormels per plant, which represents improved multiplication rate compared to previously known varieties.

As in *gladiolus* plants, the diameter of flowers and ruffledness of petals are considered for its classification, the Applicants have given the same while describing the shape and dimensions of the petals.

The hybrid was raised through conventional method of breeding. Seeds produced by hybridization of different parents were sown in the field to raise hybrid plants. After considering quality parameters some of the promising plants were selected for further multiplication. In the second year onwards, selected hybrids were multiplied and maintained vegetatively by corm and cormels. After hybridization, the hybrids are multiplied vegetatively since 1992.

The colour specifications of the flower parts distinguishing 'The Saint' from others within the same botanical and market class have been incorporated according to R.H.S. Colour Chart published by The Royal Horticultural Society, 80 Vincent Square, London S WIP 2PE, 1995. RHS Color chart is an internationally accepted color chart for identifying/referring colors of plants or plant parts. The distinguishing characteristics are compared with other varieties of same botanical and market class emphasize the distinctiveness of 'The Saint'.

The hybrid is a cross between two *gladiolus* varieties, 'Purple King' and 'Friendship'. Both 'Purple King' and 'Friendship' are of the genus *Gladiolus L* and species *Gladiolus* sp. (*Gladiolus* Hybrid). Neither of the parent varieties are patented. 'Purple King' was used as female and 'Friendship' as male to create the hybrid 'The Saint'. 'The Saint' is distinct from its parents. For example, 'Purple King' has purple flowers, rich in colour with white picottee edges, and 'Friendship' has clear pink flowers with a yellow throat. In contrast, 'The Saint' has Shrimp Red (RHS-33C) flowers with Vermilion (RHS-41A) colour on center of the lip petals.

The genotype IHBT-GH-253 ('The Saint') was bred at the Institute of Himalayan Bioresource Technology (IHBT) under the programme of development of new varieties of *Gladiolus*.

The present invention includes the novel and distinct *gladiolus* plant christened as 'The Saint' and characterized by the following combination of characteristics:

(a) The hybrid is a cross between two *gladiolus* varieties, 'Purple King' and 'Friendship'.

(b) The hybrid having Decorative type of flowers.

(c) The hybrid having flowers of Shrimp Red (RHS-33C) with Vermilion (RHS-41A) colour on center of the lip petals.

(d) The hybrid having slightly ruffled petals.

(e) The hybrid takes 84 days to flower.

(f) The average number of flower spikes/plant is 2.11.

(g) The average length of flower spikes is 108 cm.

(h) The average number of flowers per spikes is 15.9.

*Gladiolus* varieties 'Palampur Delight', 'Grace', and 'Palampur Pride' are described in copending patent applications with Ser. Nos. 10/106,150, 10/106,301, and 10/106,300, respectively, each of which is incorporated herein by reference. These varieties differ from 'Grace' in numerous aspects including flower color. For example, 'Palampur Delight' has Rose Purple (RHS-75D) flowers with Fuchsia Purple (RHS-67A) colour at the edges of the petals and Greenish White (RHS-157D) lip petal. 'Grace' has Salmon (RHS-27B) flowers with Poppy Red (RHS-40D) colour on petal edges and Chartreuse Yellow (RHS-2D) on lip petal. 'Palampur Pride' has Primerose Yellow (RHS-4 D) flowers with Fuchsia Purple (RHS-67 A) tinge on petals edges and a lip petal that is Barium Yellow (RHS-10 C) with magenta (RHS-66 C) lines. These several varieties differ in numerous other characteristics. The different characteristics can readily be determined by reading each of the patent applications.

What is claimed is:

1. A new and distinct *gladiolus* plant called 'The Saint' and substantially as shown and described.

* * * * *

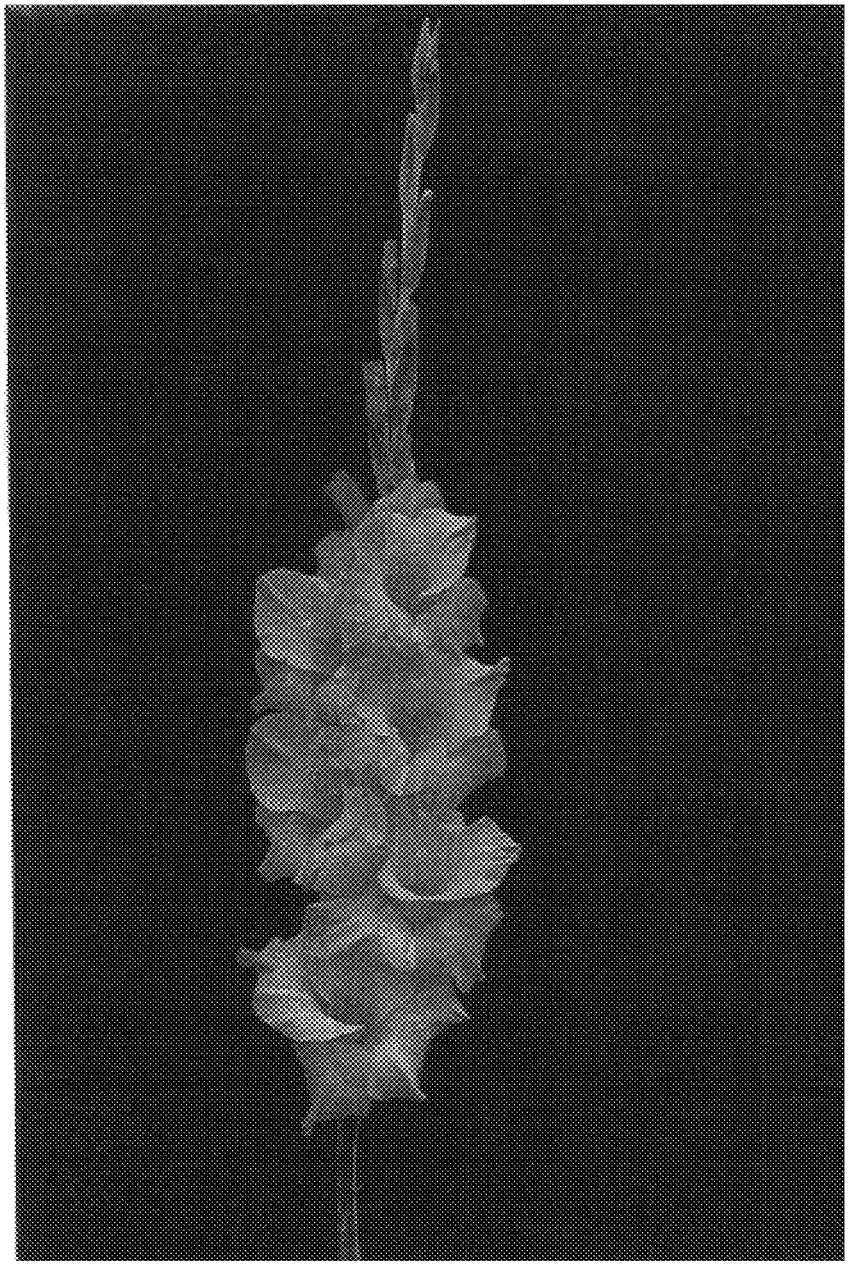
Gladiolus hybrid plant 'THE SAINT'